(12) United States Patent
Hauch et al.

(10) Patent No.: US 8,557,577 B2
(45) Date of Patent: *Oct. 15, 2013

(54) SOLID PHASE CELL ISOLATION AND/OR ENRICHMENT METHOD

(75) Inventors: Siegfried Hauch, Coppenbrügge (DE); Winfried Albert, Penzberg (DE)

(73) Assignee: Adnagen GmbH, Langenhagen (DE)

( * ) Notice: Subject to any disclaimer, the term of this patent is extended or adjusted under 35 U.S.C. 154(b) by 474 days.

This patent is subject to a terminal disclaimer.

(21) Appl. No.: 12/678,636

(22) PCT Filed: Sep. 17, 2008

(86) PCT No.: PCT/EP2008/007774
§ 371 (c)(1), (2), (4) Date: Jul. 27, 2010

(87) PCT Pub. No.: WO2009/036967
PCT Pub. Date: Mar. 26, 2009

(65) Prior Publication Data
US 2010/0285581 A1    Nov. 11, 2010

(30) Foreign Application Priority Data

Sep. 17, 2007 (EP) .................... 07018205
May 9, 2008 (EP) .................... 08008770

(51) Int. Cl.
*C12N 5/071* (2010.01)

(52) U.S. Cl.
USPC ............ 435/366; 435/325; 435/378

(58) Field of Classification Search
USPC ........... 435/325, 366, 378
See application file for complete search history.

(56) References Cited

U.S. PATENT DOCUMENTS

| 5,753,631 | A  | * | 5/1998  | Paulson et al. ............ 514/25 |
| 5,993,799 | A  | * | 11/1999 | Newgard .................. 424/93.21 |
| 2005/0256316 | A1 | * | 11/2005 | Groneberg et al. ........ 548/361.1 |
| 2006/0141512 | A1 | * | 6/2006  | Sinha et al. ............... 435/6 |

OTHER PUBLICATIONS

Definition of perfued downloaded from htpp://medical-dictionry.thefreedictionary.com/perfued on Aug. 4, 2012.*
Demel et. al., "Detection of Tumour Cells in the Peripheral Blood of Patients with Breast Cancer. Development of a New Sensitive and Specific Immunomolecular Assay," *Journal of Experimental & Clinical Cancer Research*, 23:465-468, 2004.
Morgan et. al., "The matrix effects on kinetic rate constants of antibody-antigen interactions reflect solvent viscosity," *Journal of Immunological Methods*, 217:51-60, 1998.
Milner et. al., "Ligand Binding to Anti-Fluorescyl Antibodies: Stability of the Antigen Binding Site," *Biochemistry*, 33:6221-6227, 1994.
O11e et. al., "Comparison of antibody array substrates and the use of glycerol to normalize spot morphology," *Experimental and Molecular Pathology*, 79: 206-209, 2005.
Zieglschmid et. al., "Combination of Immunomagnetic Enrichment with Multiplex RT-PCR Analysis for the Detection of Disseminated Tumor Cells," *Anticancer Research*, 15:1803-1810, 2005.

* cited by examiner

*Primary Examiner* — Susan Hanley
(74) *Attorney, Agent, or Firm* — Steptoe & Johnson LLP

(57) ABSTRACT

The present invention concerns a solid phase method for isolating and/or enriching predetermined cells from a sample. Such methods are used e.g. to isolate and enrich predetermined cells like fetal cells from a sample of maternal peripheral blood, tumor cells from a sample of body fluid or stem cells from a fluid or fluidized sample of body tissue or body fluid. The solid phase isolation method of the present invention is used for isolating predetermined cells from a sample containing such predetermined cells by binding the predetermined cells to a solid surface. According to the invention the sample is contacted with the solid surface and then removed from the solid surface, wherein the sample or a washing buffer contains a polyol during or after contacting the sample with the solid surface.

19 Claims, 9 Drawing Sheets

SOLID PHASE CELL ISOLATION AND/OR ENRICHMENT METHOD

This application is a national phase application under 35 U.S.C. §371 of International Patent Application No. PCT/EP2008/007774 filed Sep. 17, 2008, which claims priority to European Patent Application No. EP07018205.0 filed Sep. 17, 2007 and European Patent Application No. EP08008770.3 filed May 9, 2008. The entire texts of each of the above-referenced disclosures is specifically incorporated herein by reference without disclaimer.

The present invention concerns a solid phase method for isolating and/or enriching predetermined cells from a sample. Such methods are used e.g. to isolate and enrich predetermined cells like fetal cells from a sample of maternal peripheral blood, tumor cells from a sample of body fluid or stem cells from a fluid or fluidized sample of body tissue or body fluid.

The detection and analysis of rare cells in blood, bone marrow and other specimens becomes an important need in diagnostics: The detection of circulating tumor cells, including tumor stem cells and stem cells in epithelial-mesenchymal transition (EMT), and minimal residual cancer is particularly useful in oncology for improved prognosis, early detection of disease progression and therapy monitoring. Another application of such techniques is the detection and analysis of fetal cells in maternal blood that enables effective and non-invasive prenatal diagnosis of genetic and chromosomal aberrations at early stages of fetal development.

PCR based DNA analysis or RT-PCR based expression profiling are sensitive and easy to handle technologies for the detection and analysis of such rare cells. However, these technologies are affected by the fact, that contaminating leukocytes as a source of non-specific background signals due to inherent illegitimate expression or endogenous expression of tumor associated antigens are lowering the specificity of the detection of rare cells, e.g. circulating tumor cells. Similarly, DNA genotyping is not possible if the isolated tumor or fetal cells are not sufficiently pure.

The enrichment of cells from bodily specimens is an important task in many therapeutic applications, too, besides diagnostic applications, since monoclonal antibodies (or other ligands and specifiers) are available now that allow the separation of many particular cell types from sources with mixed cell populations such as blood, bone marrow and other tissues. Cell based therapies are a growing field that places serious demands on the selectivity of any cell isolation technique that is useful for that purpose. Stem cell graft engineering and immunotherapy of cancer are one of the most important applications in cellular therapy. Autologous stem cells enriched from blood or bone marrow can be used to support high dose chemotherapy regimens for a variety of malignancies.

There is a great demand for a high purity of cells isolated with cell enrichment technologies:

The usefulness of enriched stem cell products is impaired by contaminating malignant cells that might be a source for later metastases and relapses. A contamination with T-cells is the major cause of a graft versus host disease and is the primary reason for transplantation failure. Thus, an improvement of the efficacy of existing therapeutic cell enrichment technologies is a major issue that has to be urgently addressed.

There are several techniques available for the enrichment of cells from blood and other specimens. Cell sorting by FACS technology is a very specific method that can be applied to enumerate and collect rare cells for further use and analysis. However, this method is not applicable yet routinely to whole blood samples or large volumes and for large scale cell preparations. Several immunochemical methods have been developed for the enrichment of cells from fluid specimens using solid phase adsorption as for instance by immunocapturing. Monoclonal antibodies (or other adequate ligands like, for instance, aptamers or other specifiers) can be immobilised on solid surfaces like sepharose, glass, latex or plastic beads or other surfaces for through-flow column or batch applications. Although the handling of these devices is relatively convenient, recovery and purity obtained with such devices is insufficient in many cases. The use of antibody-labelled magnetic beads turned out to be quite efficient, showing good recovery rates and an enrichment rate of 4-5 $\log_{10}$. Nevertheless, this purity is still too low for expression profiling, especially if the molecular marker of interest is not over-expressed in the target cells as compared to potentially contaminating nucleated cells like leukocytes or erythropoietic stem cells. Furthermore, DNA-based genetic typing experiments to differentiate fetal from maternal cells or tumor from normal cells are generally not possible in such samples. Therefore, increasing efficacy of cell purification with solid phase immunochemical or similar devices is an urgent need not only for diagnostic but also for therapeutic applications.

There are several reasons for non-specific binding or trapping of unwanted cells during cell enrichment:

1. Although monoclonal antibodies (or other selected ligands and specifiers) should exhibit a high specificity towards the antigen (or receptor) chosen for cell separation, there may still be considerable non-specific binding to similar antigen or receptor structures.
2. Another reason for trapping unwanted cells may be physical interactions (hydrophobic or electrostatic interactions or simply mechanical trapping) with and within the solid phase/antibody (ligand or specifier) structure.
3. The target antigens or receptors chosen for cell enrichment might also be expressed on some non-target cells present in the same specimen (e.g. through illegitimate or endogenous expression).

In order to improve the performance of present days enrichment methods, these methods could be adapted to obtain better specificity by choosing a more specific antibody, ligand or specifier towards a chosen cell surface target (see 1 and 2 above) whereas non-specific carryover of non-target cells cannot be easily prevented (see 3 above). Choosing magnetic beads as carriers for antibodies, ligands or receptors instead of through-flow columns filled with beads or choosing polystyrol beads instead of sepharose are examples for possible improvements. However, most attempts for technical improvements did not lead to the purities required in many cases, and there is still an urgent need for a further reduction of the amount of non-specifically bound or trapped non-target cells, preferably by adjusting binding conditions that avoid physical interactions.

It is the object of the present invention to provide an improved isolation and/or enrichment method based on solid phase technology, that successfully removes or diminishes non-specifically bound or trapped non-target cells during solid-phase capturing like immunocapturing or ligand-capturing.

This object is solved by the solid phase isolation and/or enrichment method according to claim 1. Improvements of the inventive method are given in claims 2 to 8. Further claims 9 to 14 provide usages of the solid phase isolation and/or enrichment method according to the invention.

The present invention enables for the first time the use of solid phase immuno- or ligand-capturing procedures for important applications, e.g. genotype expression profiling, that require purified cell populations obtained from mixed cell populations like blood, bone marrow or similar specimens. The inventive method successfully removes or diminishes non-specifically bound or trapped non-target cells during solid phase isolation like solid phase immunocapturing or solid phase ligand-capturing.

The use of polyols for protein stabilisation is generally known and described. For example, glycerol is frequently used for the cryo-conservation of cells, and other polyols like mannitol are effectively used for the preservation of red blood cell preparations. Polyols (e.g. sorbitol, sucrose, trehalose) are known to be useful for protection of bacterial and eukaryotic cells during drying or heat shock procedures.

Different to these known uses of polyols in the prior art, the inventors observed to their great surprise, that polyols may not only be used for preservation of samples but are also able to reduce the background signals caused by non-specific bound or trapped non-target cells dramatically when used in solid phase cell enrichment procedures, whereas at the same time the recovery of target cells was not affected. It can be speculated that interactions of polyols with hydrophobic protein structures increase the specifity of solid phase antigen/ antibody (ligand or specifier/receptor) interactions possibly by lowering non-specific hydrophobic binding and by stabilizing the secondary and the tertiary structures of antibodies, ligands or specifiers and antigens or receptors, thereby enhancing the binding affinity and reducing non-specific interactions.

By adding polyols to the sample during solid phase cell enrichment procedures either during contacting the sample with the solid phase or in a subsequent washing step of the solid phase, it could be observed that the amount of non-specifically bound or trapped non-target cells was reduced by 99%, e.g. when using an inventive 50% (V/V) glycerol/PBS washing buffer in a manner as described e.g. in the Manual of the AdnaTest BreastCancerSelect (AdnaGen AG, Langenhagen, Germany) using antibodies against epithelial and tumor-associated antigens (EPCAM, MUC1, HER2) conjugated to magnetic beads. It further turned out that the recovery of target cells was not affected and the concentration of the target cells was very low. The addition of polyols, preferably glycerol, to samples before the cell enrichment procedure decreased the non-specifically bound or trapped non-target cell load substantially. This could also be observed at lower concentrations of glycerol, e.g. 1 to 10% (V/V). In the following, some examples of the inventive method are given.

BRIEF DESCRPTION OF THE DRAWINGS

Figure 3A:
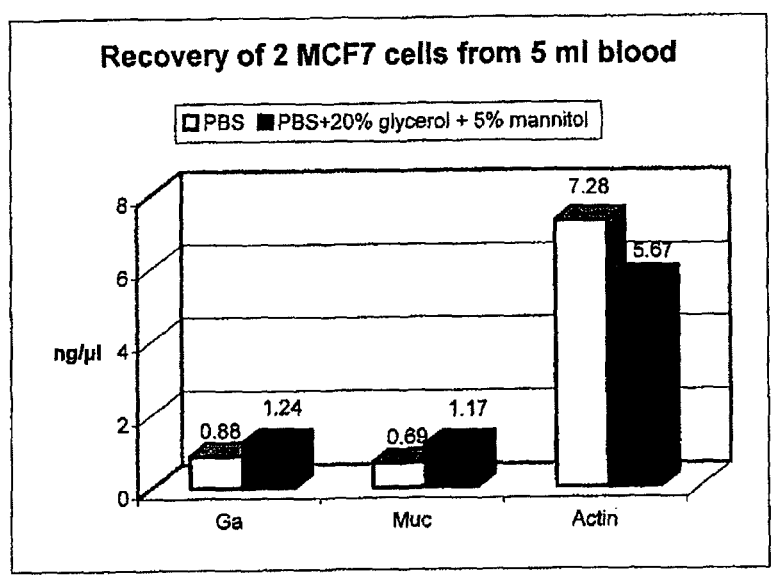
Figure 3B:
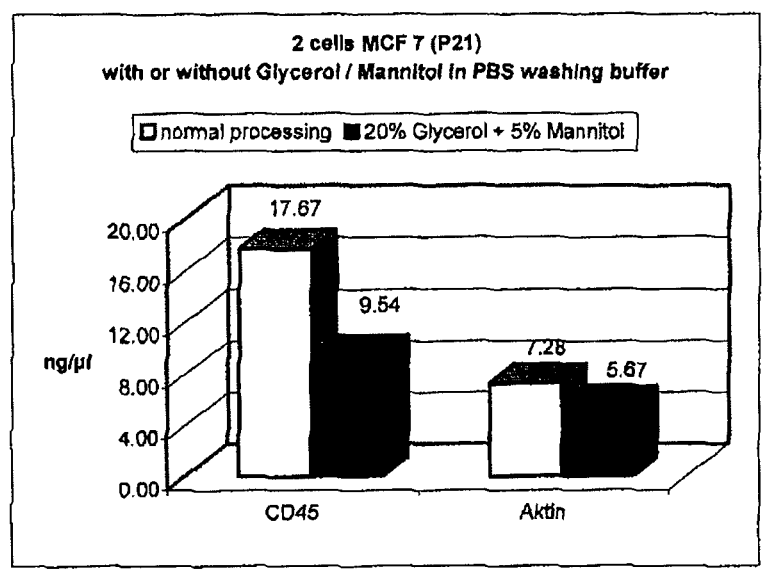
Figure 4:
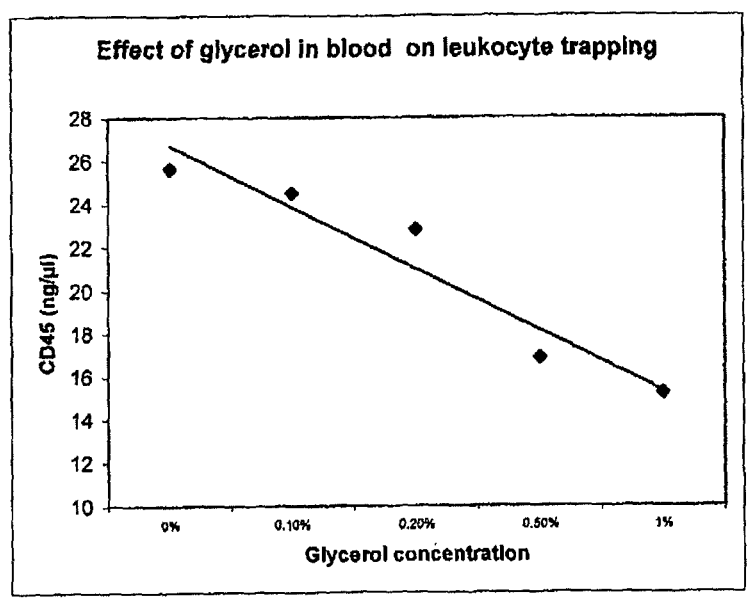
Figure 5:
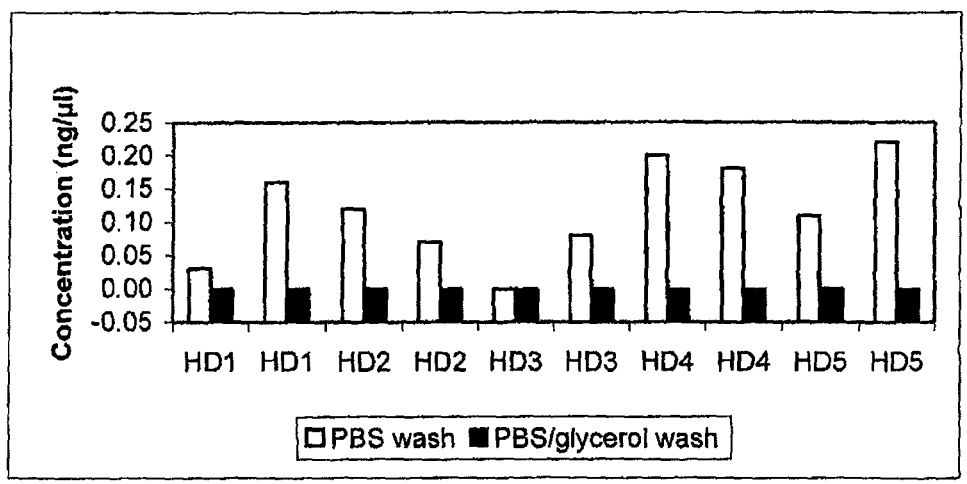
Figure 6:
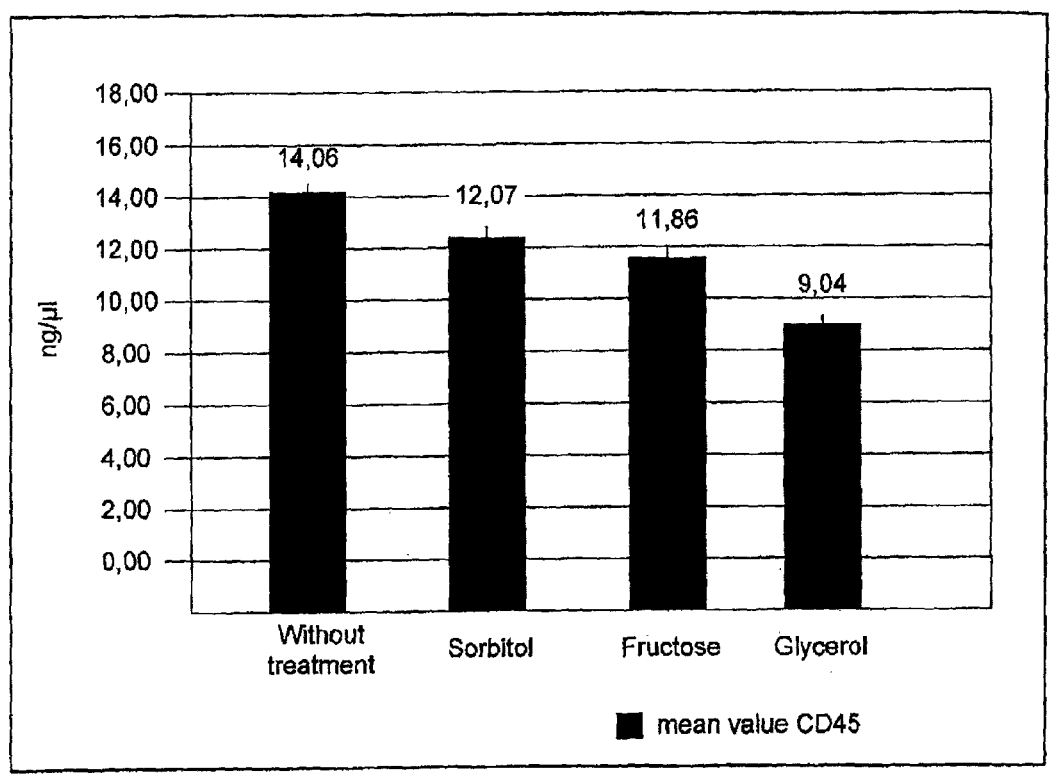
Figure 7:
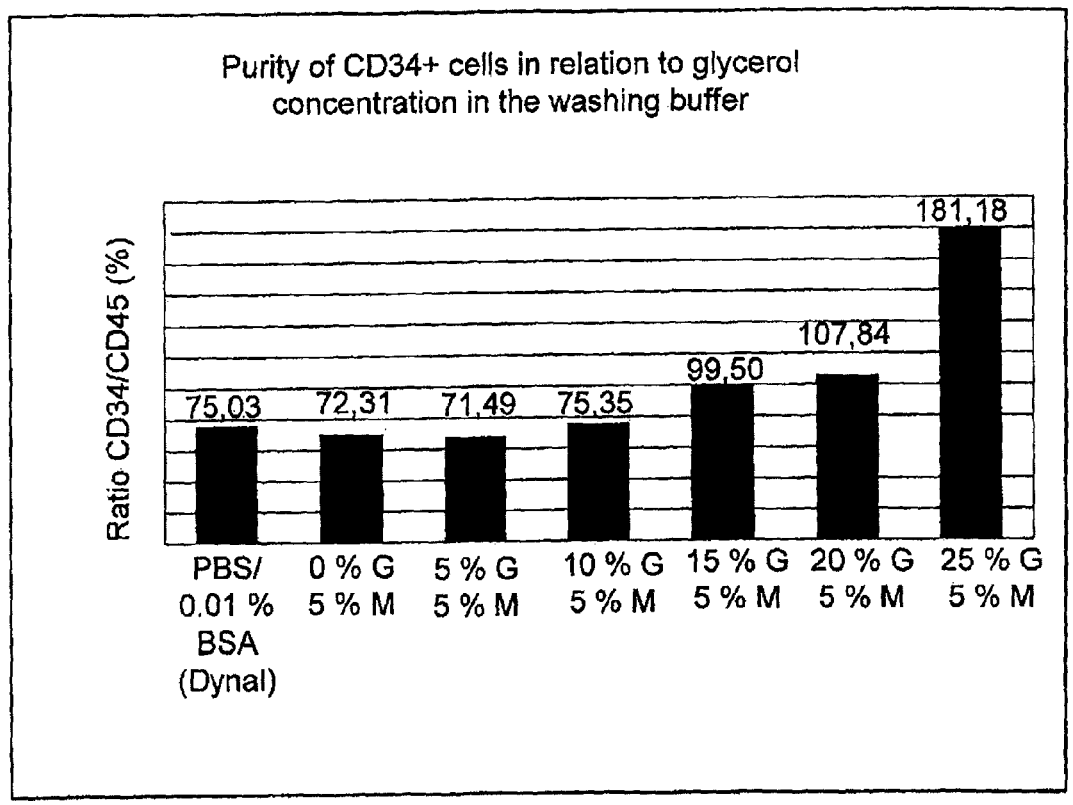
Figure 8:
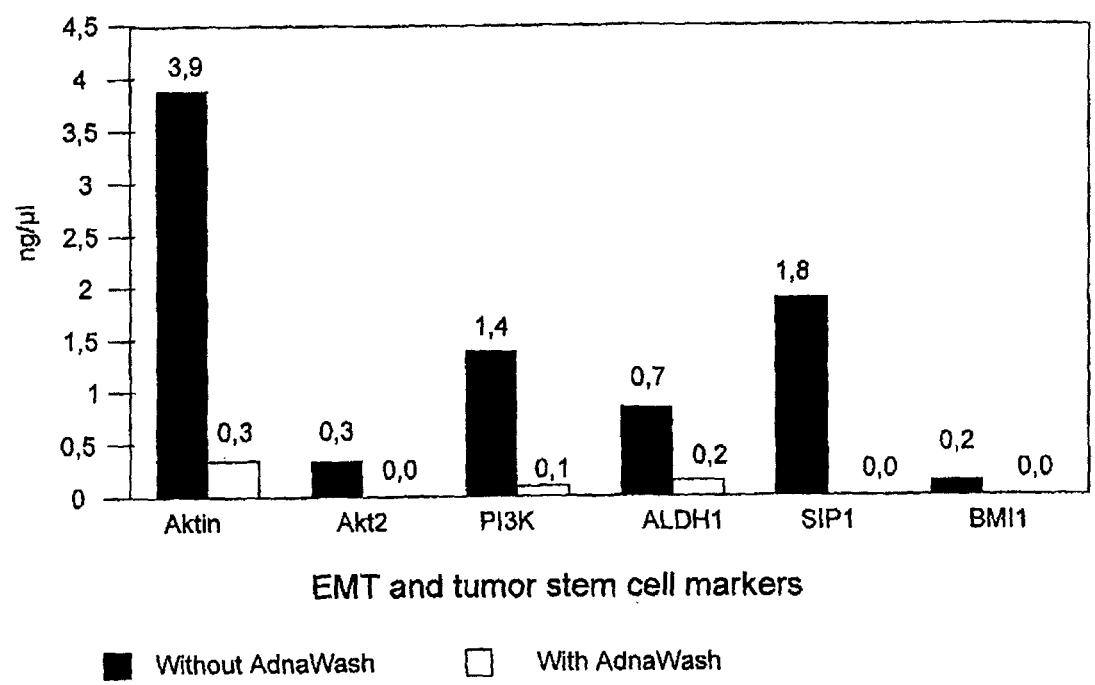

FIG. 3*a* shows the effect of a washing buffer containing 20% glycerol and 5% mannitol on the recovery of 2 MCF7 tumor cells spiked into 5 ml blood of healthy donors. FIG. 3*b* shows the decrease of CD45 mRNA levels due to the modified washing buffer;

FIG. 4 shows the effect of glycerol added to blood samples on the non-specific binding of leukocytes;

FIG. 5 shows 5 healthy donor blood samples, analyzed in duplicates for estrogen receptor (ER) expression with the AdnaTest BreastCancerDetect followed by PCR amplification of ER cDNA developed for this purpose. ER was amplified in all samples if PBS only was used during the bead washing step. The average amplicon concentrations were 0.15 ng/µl. This non-specific background activity disappeared when PBS/glycerol was used for washing;

FIG. 6 shows the influence of different polyols in the washing buffer on leukocyte background;

FIG. 7 shows the dependency of the purity of CD34(+)-stem cells purified through anti-CD34 antibody coated magnetic beads on the glycerol concentration in the washing buffer; and FIG. 8 shows the effect of polyols on leucocyte background for the isolation of tumor stem cells and EMT cells and subsequent detection of the relevant marker expression.

Examples 1-4 have been performed according to the manufacturers instructions for the detection of CTC.

EXAMPLE 1

Figure 1:
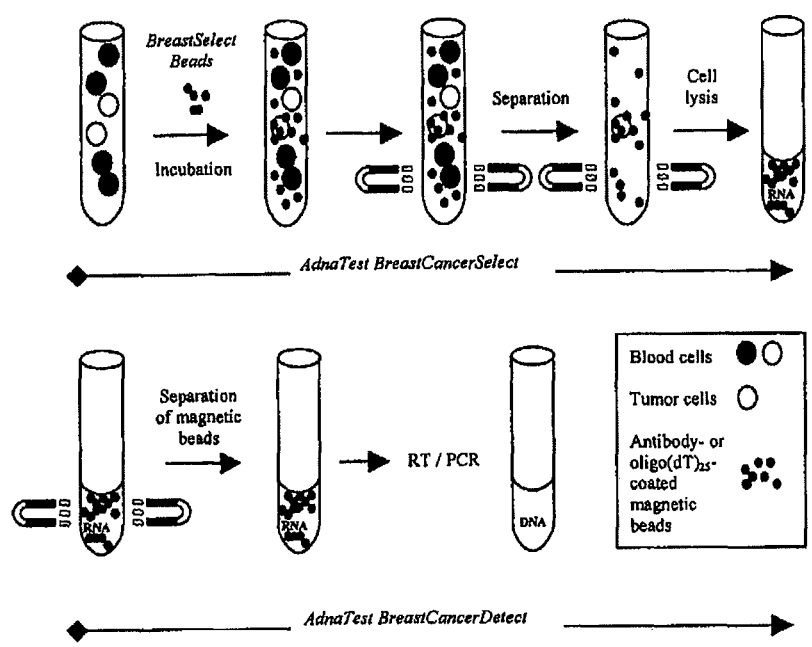
FIG. 1 shows a schematic overview of the sample preparation and analysis.
Figure 2:
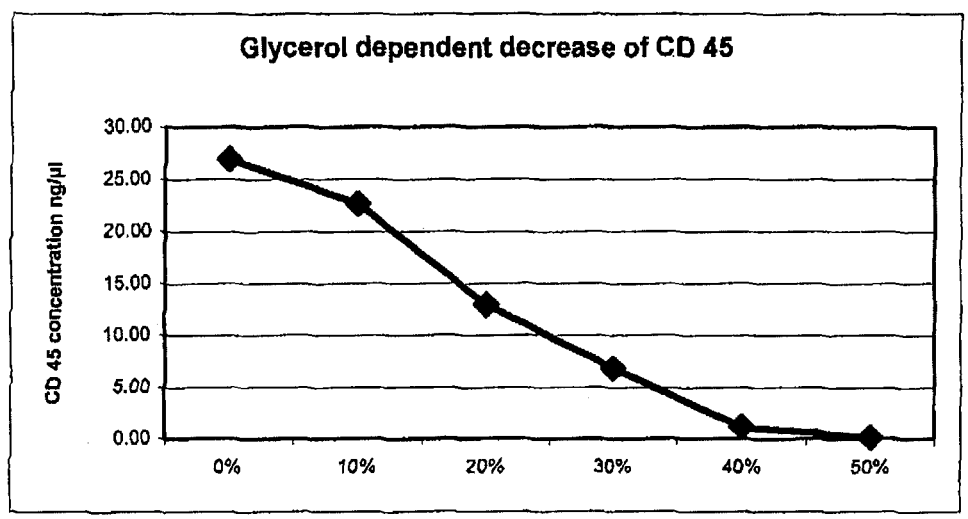
FIG. 2 shows the effect of different glycerol concentrations in the AdnaTest BreastCancerSelect washing buffer on CD45 mRNA levels.

5 ml blood samples obtained from healthy donors were processed with the AdnaTest BreastCancerSelect followed by a subsequent determination of CD45 mRNA expression. After the inoculation of the blood samples with the magnetic beads of the AdnaTest BreastCancerSelect, the subsequent washing steps were performed with PBS buffer without or with addition of different amounts of glycerol (0-50% (V/V)) (see FIG. 2). The CD45 mRNA levels decrease with increasing glycerol concentrations as shown in FIG. 1. This indicates the disappearance of contaminating leukocytes as the source of the CD45 mRNA expression.

EXAMPLE 2

2 MCF7 breast cancer cells were spiked into 5 ml blood drawn from healthy donors. The tumor cells recovered with the AdnaTest BreastCancerSelect were subsequently analysed for tumor associated mRNA markers using the AdnaTest BreastCancerDetect. This was followed by a CD45 PCR to estimate the decrease of the leukocyte contamination. After the inoculation of the blood samples with the AdnaTest BreastCancerSelect magnetic beads, the washing steps were performed with PBS containing 20% (V/V) of glycerol and 5 (W/V) mannitol. As shown in FIG. 3*a*, the recovery of the spiked cells was not impaired by the modified washing buffer. Surprisingly, the CD45 and actin mRNA concentrations decreased at the same time as the amplicon concentrations of the tumor associated markers increased, indicating a reduction of contaminating leukocytes and a higher yield of tumor cell mRNA (FIG. 3*b*).

EXAMPLE 3

Glycerol was added in different concentrations (0-1% (V/V)) to 5 ml blood samples from healthy donors. The samples were analysed using the AdnaTest BreastCancerSelect/Detect followed by a subsequent determination of CD45 mRNA expression. The CD45 amount is decreasing with increasing glycerol concentrations indicating a lower amount of bound or trapped leukocytes as shown in FIG. 4.

RT-PCR assay addressing the expression of estrogen receptor (ER) and progesterone receptor (PR) in circulating tumor cells was developed for inclusion in the AdnaTest BreastCancerSelect/Detect. Since the test for ER expression shows a relatively high background due to bound or trapped leukocytes expressing ER, it is unable to surpass a specificity of 80% at the required analytical sensitivity level (i.e. 1 or 2 tumor cells in 5 ml blood). This background activity (about 0.15 ng/µl on average), responsible for the reduction of the specificity, can be eliminated if PBS containing 30% (V/V) glycerol is used in the washing steps as shown in FIG. 5.

EXAMPLE 4

The effect of different polyols in the washing buffer on CD45 expression in the blood of healthy donors was determined in order to show the ability of different polyols to minimize unspecific background.

5 ml blood samples obtained from healthy donors were processed with AdnaTestBreastCancer Select followed by a CD45 RT-PCR. The washing steps were performed with PBS buffer containing one of said three polyols (sorbitol (10%, W/V), fructose (10% W/V), glycerol (10% V/V)). PBS buffer without additive was used as a control and for an additional final wash in all samples before cell lysis and RT-PCR. Detection of CD45 expression is an indicator for selectivity in the separation step followed by detection of CD45 as marker for residual leukocyte cells. As shown in FIG. 6, all polyols caused a reduction of CD45. Sorbitol and fructose caused about 15% and glycerol about 35% reduction of leukocyte background. Obviously, as shown with these three arbitrarily selected polyols, all polyols are suitable for the present invention.

EXAMPLE 5

In this example, the purity of CD34-positive stem cells from cord blood after immunomagnetic enrichment is determined depending on the glycerol concentration in the washing buffer (see FIG. 7).

Mononuclear cells (MNC), $3.48 \times 10^8$ cells; $9.7 \times 10^8$ cells and $2.59 \times 10^8$ cells, obtained from cord blood were re-suspended in 1 ml PBS buffer containing various concentrations of glycerol (V/V), 5% (W/V) mannitol and 0.1% BSA. After adding magnetic beads (Dynal) with anti-CD34 antibodies coupled to them, the suspension was incubated for 30 min in an overhead shaker at room temperature.

After incubation, the beads cell suspension was washed 3 times with 1 ml PBS buffer containing various concentrations of glycerol (V/V) and 5% (W/V) mannitol and 0.1% (W/V) BSA followed by lysis of the bead cell complexes in 200 µl lysis buffer (Dynal). After mRNA isolation and reverse transcription, the resulting cDNA was analyzed by PCR for CD45 (to determine trapped leukocytes) and CD34 (to determine enriched stem cells) transcripts. A ratio of the quantified PCR signal was calculated to determine the relative purity of the stem cells in relation to the glycerol concentration in the washing buffer.

As is shown in FIG. 7, glycerol/mannitol containing PBS washing buffers significantly increase the purity of the CD34 fraction (stem cell fraction) with increasing glycerol concentration in the washing buffer compared to the washing buffer without any polyol.

EXAMPLE 6

The detection of EMT and tumor cell markers is impeded by the high background signals produced by contaminating leukocytes.

To determine the effect of the AdnaWash buffer, containing the polyols glycerol (23% (V/V)) and mannitol (5% (W/V)) in PBS, healthy donor samples were processed with the AdnaTest BreastCancerSelect reagents according to instruction with and without addition of this buffer. The cDNA obtained from these samples was analyzed by PCR for the EMT markers PI3KCA, SIP1 and Akt2 as well as for the tumor stem cell markers ALDH1 and BMI1.

As shown in FIG. 8, polyols decrease the leukocyte signals interfering with EMT markers (Akt2, PI3KCA, SIP1) and tumor stem cell markers (BMI1, ALDH1) analysis due to removal of trapped leukocytes which is confirmed by the decrease of the actin signal.

By this example it is shown that trapped leukocytes express EMT and stem cell markers and produce unacceptable strong background signals. These signals could be efficiently reduced with a polyol containing washing buffer enabling a specific analysis of these markers on CTC. However, recovery of the CTC was not reduced.

The invention claimed is:

1. A solid phase isolation method for isolating predetermined target cells from a sample containing the predetermined target cells and non-target cells comprising:
   (a) contacting the sample with the solid surface to bind the predetermined target cells to the solid surface, and
   (b) washing the contacted sample from (a) with a washing buffer which removes non-bound non-target cells from the solid surface thereby isolating said predetermined target cells on the solid surface wherein the washing buffer comprises at least one polyol selected from sorbitol, trehalose, sucrose, mannitol, fructose, malitol, lacitol and xylitol, wherein the sample contains the polyol at least during one of (a) contacting the sample with the solid surface or (b) washing.

2. The method according to claim 1, wherein before or during contacting the sample with the solid surface, the polyol is added to the sample.

3. The method according to claim 1, wherein a washing buffer for washing the solid surface contains the polyol.

4. The method according to claim 1, wherein the polyol is added to the sample or contained in the washing buffer in a final concentration (W/V or V/V) selected from least 1%, at least 10%, at least 20%, at least 30%, at least 50%, or at least 60%.

5. The method according to claim 1, wherein the solid surface is selected from a gel surface, sepharose surface, glass surface, latex surface, ceramics surface, metal surface and plastic surface.

6. The method according to claim 1, wherein the solid surface is the surface of magnetic beads.

7. The method according to claim 1, wherein ligands or antibodies are immobilized on the solid surface, which ligands or antibodies specifically bind to the predetermined cells.

8. The method according to claim 1, wherein the predetermined target cells are rare cells.

9. The method according to claim 1, wherein the predetermined target cells are fetal cells, and the sample is maternal peripheral blood.

10. The method according to claim 1, wherein the predetermined target cells are tumor cells from cell suspensions including at least one of peripheral blood, bone marrow, urine, ascites, or sputum from a patient.

11. The method according to claim 1, wherein the predetermined target cells are stem cells, and the sample is a body fluid and/or from a tissue sample from a human being.

12. The method according to claim 1, wherein the predetermined target cells are tumor cells and/or epithelial-mesenchymal transition (EMT) cells, and the sample is a body fluid and/or from a tissue sample.

13. The method according to claim 1, wherein the predetermined target cells are stem cells, and the sample is a body fluid and/or from a tissue sample from a human being.

14. The method according to claim 1, wherein the predetermined target cells are tumor stem cells and/or EMT cells, and the sample is a body fluid and/or from a tissue sample.

15. A solid phase enrichment method for enriching predetermined target cells from a sample containing the predetermined target cells and non-target cells comprising:
   (a) contacting the sample with the solid surface to bind the predetermined target cells to the solid surface, and
   (b) washing the contacted sample from (a) with a washing buffer which removes non-bound non-target cells from the solid surface thereby enriching said predetermined target cells on the solid surface wherein the washing buffer comprises at least one polyol selected from sorbitol, sucrose, mannitol, fructose, malitol, lacitol and xylitol, wherein the sample contains the polyol at least during one of (a) contacting the sample with the solid surface or (b) washing.

16. The method according to claim 15, wherein before or during contacting the sample with the solid surface, the polyol is added to the sample.

17. The method according to claim 15, wherein a washing buffer for washing the solid surface contains the polyol.

18. The method according to claim 15, wherein the predetermined target cells are fetal cells, and the sample is maternal peripheral blood.

19. The method according to claim 15, wherein the predetermined target cells are tumor cells and the sample is a cell suspension including at least one of peripheral blood, bone marrow, urine, ascites, or sputum from a patient.

* * * * *